United States Patent [19]

Leland et al.

[11] Patent Number: 4,911,889

[45] Date of Patent: Mar. 27, 1990

[54] METHODS FOR SANITIZING MATERIALS UTILIZING SUPERHEATED STEAM

[75] Inventors: Bernnie J. Leland, Westchester; Keith J. Hanley, Cincinnati; Paul D. Leis, Jr., Hamilton; Katherine L. Moore, Cincinnati, all of Ohio

[73] Assignee: The Procter & Gamble Company, Cincinnati, Ohio

[21] Appl. No.: 97,238

[22] Filed: Sep. 16, 1987

[51] Int. Cl.$^4$ .............................................. A61L 2/06
[52] U.S. Cl. .......................................... 422/26; 47/58; 47/DIG. 9; 422/32
[58] Field of Search .......... 422/26, 32; 47/58, DIG. 9

[56] References Cited

U.S. PATENT DOCUMENTS

| | | |
|---|---|---|
| 1,902,625 | 3/1933 | Dunham . |
| 2,260,710 | 10/1941 | Gschwind . |
| 2,635,943 | 4/1953 | MacMasters ........................ 422/26 |
| 3,415,613 | 12/1968 | Wallden . |
| 3,436,170 | 4/1969 | Lodge . |
| 3,564,723 | 2/1971 | Passey et al. ........................ 34/22 |
| 3,721,527 | 3/1973 | Lodige et al. . |
| 3,808,093 | 4/1974 | Hedstrom ........................... 162/100 |
| 3,992,147 | 11/1976 | Christian et al. ..................... 422/32 |
| 3,994,685 | 11/1976 | Lodige et al. ..................... 422/32 X |
| 4,043,049 | 8/1977 | Hedstrom ............................. 34/10 |
| 4,062,646 | 12/1977 | Lodige et al. ..................... 422/32 X |
| 4,234,537 | 11/1980 | Hersom et al. ....................... 422/26 |
| 4,709,487 | 12/1987 | Akao et al. ........................... 34/10 |
| 4,780,279 | 10/1988 | Enos ..................................... 422/32 |

FOREIGN PATENT DOCUMENTS

| | | |
|---|---|---|
| 61305 | 9/1982 | European Pat. Off. . |
| 94448 | 11/1983 | European Pat. Off. . |
| 105195 | 4/1984 | European Pat. Off. . |
| 196464 | 10/1986 | European Pat. Off. . |

OTHER PUBLICATIONS

"Effect of Heat, Ethyleneoxide and Gamma Radiation on Psyllium Husk", Gopal et al., *Indian J. Pharm. Sci.,* 49(2), pp. 75–76 (Mar.–Apr. 1987).
"Superheated Steam Sterilizing System for Powder and Granules"; Kikkoman Corp. brochure.
"Thermal Disinfestation of Cereal Grains"; Bulletin No. 69 by Niro Atomizer.
"New Ways of Drying and Processing Sugar Beet Pulp"; by Swedish Exergy Techology, Inc.
Brochure from Swedish Exergy Technology, Inc.

*Primary Examiner*—Barry S. Richman
*Assistant Examiner*—Jill Johnston
*Attorney, Agent, or Firm*—Kim William Zerby; Douglas C. Mohl; Richard C. Witte

[57] ABSTRACT

Processes for sanitizing materials, especialy psyllium, using superheated steam maintained at a relatively constant low level of superheat. These processes are very effective for sanitizing materials, and can produce commercially sterile materials. Furthermore, these processes can be used to produce highly pure, commercially sterile psyllium having substantially intact cell structure.

17 Claims, No Drawings

METHODS FOR SANITIZING MATERIALS UTILIZING SUPERHEATED STEAM

BACKGROUND OF THE INVENTION

The present invention relates to highly effective, novel processes for sanitizing materials, especially hydrophilic materials (e.g., psyllium fiber), using superheated steam. The present invention further relates to novel apparatuses for sanitizing materials, especially hydrophilic materials. Finally, the present invention relates to high purity sanitized psyllium having improved aesthetics.

Superheated steam sterilization equipment and processes are known. For example, Kikkoman Corporation (Tokyo, Japan) utilizes a superheated steam sterilizing system to sanitize a variety of materials such as black pepper, paprika, buckwheat flour, and fish flour. This system involves the use of a superheater to heat steam to a high level of superheat, and then this superheated steam is blown through a pipe along with the material to be sanitized. The level of superheat in this system is not maintained constant throughout the system, and thus decreases constantly and substantially from the time it contacts the material until it is separated from the material.

It is also known that superheated steam can be utilized to dry materials. For example, Swedish Exergy Technology, Inc. (Gothenburg, Sweden) utilizes superheated steam to dry materials such as sugar beet pulp. This process converts a high moisture content material into a low moisture content material.

The present invention relates to the discovery of improved processes for sanitizing materials using superheated steam maintained at a relatively constant low level of superheat. It is therefore an object of the present invention to provide novel processes for sanitizing materials utilizing such superheated steam. It is also an object to provide processes having improved effectiveness for sanitizing materials. It is a further object to provide processes for sanitizing large quantities of materials. A still further object is to provide processes which are especially well suited for sanitizing hydrophilic materials such as psyllium. An object is also to provide processes for sanitizing psyllium fiber, and to provide sanitized psyllium fiber prepared by such processes. This sanitized psyllium fiber has high purity and improved aesthetic characteristics, and typically has substantially intact cell structure. A further object is to provide highly pure psyllium, especially commercially sterile psyllium; and also to provide psyllium having reduced oil content and/or reduced protein content and/or reduced ash content. Another object of the present invention is to provide apparatuses useful for carrying out the processes of the present invention.

These and other objects of the present invention will become readily apparent from the detailed description which follows.

All percentages and ratios used herein are by weight unless otherwise specified.

SUMMARY OF THE INVENTION

The present invention relates to processes for sanitizing materials utilizing superheated steam. These processes comprise the steps of: (1) contacting a low moisture content (preferably within the range of from about 5% to about 30% moisture content) material in need of sanitization with superheated steam at a low level of superheat; (2) maintaining the steam at a relatively constant low level of superheat while in contact with the material being sanitized; and (3) separating the superheated steam from the sanitized material. The moisture content of the sanitized material is preferably about the same as the moisture content of the material in need of sanitization.

The present invention also relates to psyllium sanitized according to the processes of the present invention. Furthermore, the present invention relates to highly pure, commercially sterile psyllium having substantially intact cell structure.

Finally, the present invention also relates to apparatuses for carrying out the processes of the present invention which are especially useful for sanitizing hydrophilic materials such as psyllium. Such apparatuses comprise: (1) moisture and pressure tight means for introducing low moisture content material in need of sanitization into a superheated steam system under pressure and at low levels of superheat; (2) means for maintaining the temperature of the superheated steam at about a relatively constant low level of superheat during the sanitization process (preferably by means of jacketed or traced tubes); and (3) means for separating the sanitized material from the superheated steam without steam condensation coming in contact with the sanitized material.

DETAILED DESCRIPTION OF THE INVENTION

Processes For Sanitizing Materials Utilizing Steam at Relatively Constant Low Levels of Superheat The present invention relates to processes for sanitizing low moisture content materials by utilizing superheated steam which is maintained at relatively constant low levels of superheat during the sanitization process. The moisture content of the material being sanitized is not greatly changed during the sanitization, with the sanitized material preferably having a moisture content of about ±20% of the moisture content of the material before sanitization, preferably ±10%, more preferably ±5%, and most preferably having essentially the same moisture content ±1%. The measurement and control of moisture content in superheated steam systems is well known, and such techniques are equally applicable to use in sanitizing materials according to the present invention.

The low moisture content materials which may be sanitized by the present processes have moisture contents before sanitization of less than about 30%, preferably within the range of from about 1% to about 25%, more preferably within the range of from about 5% to about 20% and most preferably within the range of from about 5% to about 15%. If psyllium material is to be sanitized by the present process, such psyllium materials before sanitization typically have a moisture content of about 10%. However, for purposes of the present processes, in order to avoid producing sanitized products such as psyllium with too low a moisture content it may be desirable to include a step prior to sanitization whereby the moisture content of the material in need of sanitization is slightly raised.

The low moisture content materials which may be sanitized by the present processes include any materials which are in need of sanitization (i.e., have unacceptably high microbial contamination) and which are capable of being contacted with superheated steam. Obviously, materials which are substantially negatively affected by the high temperatures and/or contact with steam involved in the present processes cannot be sanitized utilizing these processes. Preferably, the material to be sanitized are particulant materials capable of being blown through a system while in contact with the superheated steam which is maintained at a constant low level of superheat. Preferred are hydrophilic materials, and especially psyllium. Such materials are readily chosen by one skilled in the art.

The processes of the present invention are particularly well suited for sanitizing hydrophilic material, and are especially well suited for sanitizing psyllium. Psyllium materials come from psyllium seed, from plants of the Plantago genus. Various species such as *Plantago lanceolate, P. rugelii,* and *P. major* are known. Commercial psyllium includes the French (black; *Plantago indica*), Spanish (*P. psyllium)* and Indian (blond; *P. ovata*). Indian (blond) psyllium is preferred for use herein. Intact or macerated psyllium seeds can be sanitized by the present invention; however, it is desirable to sanitize only the seed coat which has been removed from the seed by slight mechanical pressure.

The superheated steam utilized in the processes herein is required to be heated to a low level of superheat prior to contact with the material in need of sanitization, and to be maintained at a relatively constant low level of superheat while in contact with the material being sanitized. Preferably, the superheated steam is heated to and maintained at a low level of superheat temperature within about 1° C. to about 40° C., more preferably within about 5° C. to about 30° C., and most preferably within about 5° C. to about 20° C. of the boiling point temperature of the steam at the pressure being utilized (this boiling point temperature is also known as the "steam saturation temperature"). Preferably, the low level of superheat is maintained almost constant during the processes, preferably varying less than about ±5° C., and more preferably varying less than about ±3° C. The preferred pressure for the superheated steam is within the range of from about 1.5 to about 5.0 bars absolute pressure, more preferably from about 1.75 to about 3.0 bars absolute pressure, and most preferably from about 1.8 to about 2.3 bars absolute pressure. If psyllium is being sanitized, a pressure of about 2.0 bars absolute pressure and a relatively constant level of superheat of from about 5° C. to about 15° C. is most preferred.

The preferred process of the present invention involves blowing superheated steam and the material to be sanitized through a pressurized system which maintains a relatively constant low level of superheat. The preferred method for maintaining the superheated steam at a relatively constant low level of superheat in such a blowing process is by means of jacketed or traced tubes, preferably steam jacketed or traced tubes.

The preferred equipment for such blowing processes consist of steam jacketed tubes, a cyclone, and steam circulating fans interconnected by ducting and arranged in a closed loop system. Low pressure superheated steam at a low level of superheat is circulated through the system and the material to be sanitized is introduced into the superheated steam flow (referred to herein as the "transport steam") by means of a pressure tight feeding valve (preferably a moisture and pressure tight feeding valve, especially when sanitizing hydrophilic materials such as psyllium). The material to be sanitized is carried along with the superheated transport steam through the steam jacketed tubes. As the transport steam and the suspended particles of material to be sanitized pass through the tubes, this transport steam is maintained at a relatively constant low level of superheat by a medium outside the transport tube. The material is passed through the jacketed/traced transport tubes (one or more of them as desired to obtain the appropriate residence time for the particles and to obtain the appropriate amount of microbial kill during the sanitization), and then the sanitized material is separated from the transport steam. This may be achieved by a high efficiency cyclone followed by discharge of the material from the system by means of a pressure tight discharge valve. However, it is greatly preferred for sanitization of hydrophilic materials such as psyllium that the separation be achieved by a process which does not permit any condensed water to come in contact with the sanitized material. A novel apparatus especially well suited for sanitizing hydrophilic materials, especially psyllium, is described in detail hereinafter.

A variety of other variables are present in the preferred blown superheated steam system as described hereinbefore, but the selection of appropriate conditions according to the material being sanitized are readily made by one skilled in the art. For example, conditions for steam sanitization of psyllium by such processes typically utilize the following condition parameters: steam density within the range of from about 0.062 to about 0.083 lbs/ft$^3$; flow rate within the range of about 2000 to 5000 ft/minute (approximately 10 to about 25 m/sec); from about 2.2 to about 7.4 lbs steam/lbs psyllium; steam residence time of from about 1.9 to about 4.8 seconds; and a psyllium fiber residence time of from about 3 to about 40 seconds. Of these variables, the residence time for the material being sanitized has the most impact on the optimization of the sanitization and the aesthetics of the material. Residence time can be increased or decreased as desired, for example, by changing the length of the system and/or varying the flow rate of the system.

While not intending to be bound by theory, it is believed that the improved efficacy of the processes of the present invention for sanitizing materials may be explained as follows. Prior art systems are believed to sensibly heat the material being sanitized and sensibly cool the steam. (The term "sensibly", as used herein, means the temperature of the material or steam changes as energy is added to or taken away from the material or steam). This results in little, if any, condensation of steam onto the material being sanitized.

By contrast, the present processes use low levels of superheat and these low levels are maintained relatively constant. It is believed that by the processes herein the material is sensibly heated while the steam is latently cooled. (The term "latently", as used herein, means the temperature of the steam does not change as energy is added to or taken away from the steam, for example, as occurs when steam condenses or vaporizes). The net result is that some of the steam condenses on the material being sanitized, thereby temporarily raising the moisture content of the material by some small but significant amount from the standpoint of more effectively killing the microbes present in the material. As the material passes further through the system, the moisture content of the material (typically) is again lowered to about the incoming moisture content level.

This combination of high temperature plus increased moisture phase appears to be responsible for the greatly improved sanitization effectiveness observed for the present processes. In fact, commercially sterile material is possible by utilizing the present processes. Furthermore, these processes eliminate contaminants which may be found in raw psyllium, including volatile contaminants which may be stripped away by steam, and thus provides highly pure psyllium with improved product aesthetics (such as improved taste). Furthermore, this process permits the production of highly pure psyllium having substantially intact cell structure.

Steam Sanitized Psyllium

The present invention further relates to psyllium fiber which is sanitized by the processes described hereinbefore. Such psyllium fiber has improved purity and/or aesthetics versus psyllium sanitized by art known methods (such as by sanitization with ethylene oxide; by extrusion as described, for example, in European Patent Application No. 105,195, published Apr. 11, 1984, by G. D. Searle & Co.; and by aqueous isopropanol/hydrogen peroxide sanitization as described for example in U.S. Pat. No. 3,992,147, to Christian et al, issued Nov. 16, 1976, the disclosures of both these patent specifications being incorporated herein by reference in their entirety), and may be processed such that it retains a substantially intact cell structure.

The present invention thus includes high purity, commercially sterile psyllium fiber having intact cell structure. High purity as it relates to the psyllium fiber of the present invention means psyllium fiber having reduced contaminants, including reduced oil content, reduced protein content (especially reduced higher molecular weight protein content), and reduced ash content.

Apparatuses For Steam Sanitizing Materials

In order to process materials (especially hydrophilic materials) according to the present invention by using the steam flow system preferred and described hereinbefore, it is highly desirable to utilize the following apparatuses. These apparatuses of the present invention comprise: (1) moisture and pressure tight means for introducing low moisture content materials (especially hydrophilic materials such as psyllium) in need of sanitization into a superheated steam system (especially a superheated steam flow system) under pressure and at low levels of superheat; (2) means for maintaining the temperature of the superheated steam at about a relatively constant low level of superheat during the sanitization process (preferably by means of traced or jacketed tubes, especially steam jacketed or traced tubes); and (3) means for separating the sanitized material from the superheated steam without steam condensation coming in contact with the sanitized material.

The preferred means for separating the steam and sanitized materials are means whereby hot air is contacted with the sanitized material immediately following sanitization. Preferably, the sanitized material is separated from the transport steam by a cyclone separator and a rotary pressure tight discharge valve, and then the material leaving the discharge valve is flooded with air at the saturation temperature corresponding to the transport steam pressure. The sanitized material is then blown into a second cyclone separator which separates the steam/air from the material. The material then falls into the product collector.

The following example further describes and demonstrates an embodiment within the scope of the present invention. The example is given solely for the purpose of illustration and is not to be construed as a limitation of the present invention as many variations thereof are possible without departing from the spirit and scope.

EXAMPLE I

Steam Sterilization of Psyllium

Raw psyllium husk (density=0.28 grams/mg; moisture content=approximately 10%; 40,000 to 170,000 colony forming units per gram) is fed into a superheated steam system which utilizes steam jacketed tubes to maintain the temperature of the superheated steam relatively constant ($\pm 5°$ C.) throughout the system. A pressure tight inlet rotary valve followed by an inlet screw feeder introduces the raw psyllium husk at a rate of 100 kg/hour into a superheated transport steam flow under the following conditions: 2.0 bars absolute pressure; 121° C. saturated steam temperature; 131° C. total steam temperature (10° C. of super-heat); steam density=0.0695 lbs/cubic ft; flow rate=2000 ft/minute (10 m/sec). The steam jacketed tubing consists of 6 tubes (3.5 inches internal diameter; 4.0 inches outer diameter; 26.2 ft long) having a heat transfer area of 142 ft$^2$ (high pressure steam jacketing is as follows: 17,424 BTU/hour; pressure=250 psig; 30 lbs/hour steam flow rate). The steam residence time for these conditions is 4.8 sec, and the psyllium residence time for these conditions is approximately 2-3 times the steam residence time. The psyllium is separated from the super-heated steam in a high efficiency cyclone, discharged from the cyclone by means of a pressure tight rotary discharge valve, and collected.

Improved product quality and ease of processing the sanitized psyllium is achieved if, rather than collecting the sanitized psyllium at this point, the psyllium leaving the pressure tight rotary discharge valve is flooded with air at approximately 120° C. The sanitized psyllium is then blown into a second cyclone separator which separates the steam/air from the sanitized psyllium which falls into a product collector.

The resulting sanitized psyllium husk has the following characteristics: approximately 10% moisture content; less than about 100 colony forming units per gram (i.e., commercially sterile). The psyllium has very good aesthetics, is highly pure, and has substantially intact cell structure.

What is claimed is:

1. A process for sanitizing materials comprising the steps of:
  (a) contacting, by introducing into a superheated steam flow, a low moisture content material in need of sanitization with superheated steam at a low level of superheat within from about 1° C. to about 40° C. above the steam saturation temperature;
  (b) maintaining the steam at a relatively constant low level of superheat within from about 1° C. to about 40° C. above the steam saturation temperature while in contact with the material being sanitized; and
  (c) separating the sanitized material from the superheated steam.

2. The process for sanitizing materials according to claim 1 wherein the superheated steam is under a pressure within a range of from about 1.5 to about 5.0 bars absolute pressure.

3. The process for sanitizing materials according to claim 2 wherein the low moisture content material in need of sanitization has a moisture content of less than about 30%.

4. The process for sanitizing materials according to claim 1 wherein the material in need of sanitization is contacted with a stream of superheated steam at low levels of superheat within from about 5° C. to about 30° C. above the steam saturation temperature under pressure within a range of from about 1.75 to about 3.0 bars absolute pressure; and said stream of superheated steam is maintained at a relatively constant low level of superheat within from about 5° C. to about 30° C. above the steam saturation temperature during contact with the material being sanitized by use of jacketed or traced tubes.

5. A process for sanitizing hydrophilic materials comprising the steps of:
   (a) contacting, by introducing into a superheated steam flow, a low moisture content hydrophilic material in need of sanitization with a stream of superheated steam at a low level of superheat within from about 1° C. to about 40° C. above the steam saturation temperature under pressure;
   (b) maintaining the steam at a relatively constant low level of superheat within from about 1° C. to about 40° C. above the steam saturation temperature while in contact with the hydrophilic material being sanitized; and
   (c) separating the sanitized hydrophilic material from the superheated steam.

6. The process for sanitizing hydrophilic materials according to claim 5 wherein the pressure of the superheated steam is within the range of from about 1.5 to about 5.0 bars absolute pressure.

7. The process for sanitizing hydrophilic materials according to claim 6 wherein the low moisture content material in need of sanitization has a moisture content of less than about 30%.

8. The process for sanitizing hydrophilic materials according to claim 7 wherein the sanitized material has a moisture content within about ±20% of the moisture content of the material in need of sanitization.

9. The process for sanitizing hydrophilic materials according to claim 7 wherein the hydrophilic material in need of sanitization is contacted with the stream of superheated steam at a low level of superheat within from about 5° C. to about 30° C. above the steam saturation temperature under pressure within a range of from about 1.5 to about 5.0 bars absolute pressure; and said stream of superheated steam is maintained at a relatively constant low level of superheat within from about 5° C. to about 30° C. above the steam saturation temperature during contact with the material being sanitized by use of jacketed or traced tubes.

10. A process for sanitizing psyllium fiber comprising the steps of:
    (a) contacting, by introducing into a superheated steam flow, a low moisture content psyllium fiber in need of sanitization with a stream of superheated steam at a low level of superheat within from about 1° C. to about 40° C. above the steam saturation temperature under pressure;
    (b) maintaining the steam at a relatively constant low level of superheat within from about 1° C. to about 40° C. above the steam saturation temperature while in contact with the psyllium fiber being sanitized; and
    (c) separating the sanitized psyllium fiber from the superheated steam.

11. The process for sanitizing psyllium fiber according to claim 10 wherein the pressure of the superheated steam is within the range of from about 1.5 to about 5.0 bars absolute pressure.

12. The process for sanitizing psyllium fiber according to claim 11 wherein the low moisture content psyllium fiber in need of sanitization has a moisture content of less than about 30%.

13. The process for sanitizing psyllium fiber according to claim 12 wherein the sanitized psyllium fiber has a moisture content within about ±20% of the moisture content of the psyllium fiber in need of sanitization.

14. The process for sanitizing psyllium fiber according to claim 12 wherein the psyllium fiber in need of sanitization is blown with the stream of super-heated steam at a low level of superheat within from about 5° C. to about 30° C. above the steam saturation temperature under pressure within a range of from about 1.5 to about 5.0 bars absolute pressure; and said stream of superheated steam is maintained at a relatively constant low level of superheat within from about 5° C. to about 30° C. above the steam saturation temperature during contact with the psyllium fiber being sanitized by use of jacketed or traced tubes.

15. A process for sanitizing psyllium fiber comprising the steps of:
    (a) blowing psyllium fiber, having a moisture content within the range of from about 5% to about 15%, in need of sanitization with a stream of superheated steam at a low level of superheat within from about 1° C. to about 40° C. above the steam saturation temperature under pressure within the range of from about 1.5 to about 5.0 bars absolute pressure;
    (b) maintaining the steam at a relatively constant low level of superheat within from about 1° C. to about 40° C. above the steam saturation temperature while in contact with the psyllium fiber being sanitized; and
    (c) separating the sanitized psyllium fiber from the super-heated steam, said sanitized psyllium having a moisture content within the range of from about 5% to about 15%.

16. The process for sanitizing psyllium fiber according to claim 15 wherein the psyllium fiber in need of sanitization is blown with the stream of superheated steam at a low level of superheat within from about 5° C. to about 20° C. above the steam saturation temperature under pressure within a range of from about 1.5 to about 3.0 bars absolute pressure; and said stream of superheated steam is maintained at a relatively constant low level of superheat within from about 5° C. to about 20° C. above the steam saturation temperature during contact with the psyllium fiber being sanitized.

17. The process for sanitizing psyllium fiber according to claim 16 wherein the superheated steam is maintained at a relatively constant low level of superheat by use of jacketed or traced tubes.

* * * * *